United States Patent
Dyrberg et al.

(10) Patent No.: US 6,274,549 B1
(45) Date of Patent: Aug. 14, 2001

(54) TREATMENT OF TYPE 1 DIABETES

(75) Inventors: Thomas Dyrberg, Hellerup; Anne Worsaae, Lyngby, both of (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 09/319,138

(22) PCT Filed: Jul. 1, 1996

(86) PCT No.: PCT/DK96/00297

§ 371 Date: Dec. 19, 1997

§ 102(e) Date: Dec. 19, 1997

(87) PCT Pub. No.: WO97/02043

PCT Pub. Date: Jan. 23, 1997

(30) Foreign Application Priority Data

Jun. 30, 1995 (DK) .................................................. 0765/95

(51) Int. Cl.$^7$ ............................ A61K 38/28; C07K 14/62
(52) U.S. Cl. ...................... 514/3; 514/2; 514/4; 530/303; 424/184.1
(58) Field of Search ............................ 514/2–4; 530/303; 424/184.1

(56) References Cited

U.S. PATENT DOCUMENTS 5,422,339   6/1995   Eisenbarth ................................ 514/3

FOREIGN PATENT DOCUMENTS

92/06704   4/1992   (WO) .
95/24216   9/1995   (WO) .
97/09061   3/1997   (WO) .

OTHER PUBLICATIONS

Ziegler et al., "Prophylactic Insulin Treatment in Relatives at High Risk For Type 1 Diabetes", Diabetes/Metabolism Reviews, vol. 9, No. 4, 289–293 (1993), pp. 289–293.

*Primary Examiner*—Bennett Celsa
(74) *Attorney, Agent, or Firm*—Reza Green, Esq.; Valeta A. Gregg, Esq.

(57) ABSTRACT

Insulin analogues which are substantially devoid of hypoglycemic effect can be used for treating of delaying the onset of type 1 diabetes or ameliorating of an early stage thereof in a mammal at risk of developing diabetes.

8 Claims, 5 Drawing Sheets

TREATMENT OF TYPE 1 DIABETES

CROSS-REFERENCE TO RELATED APPLICATIONS

Figure 1:
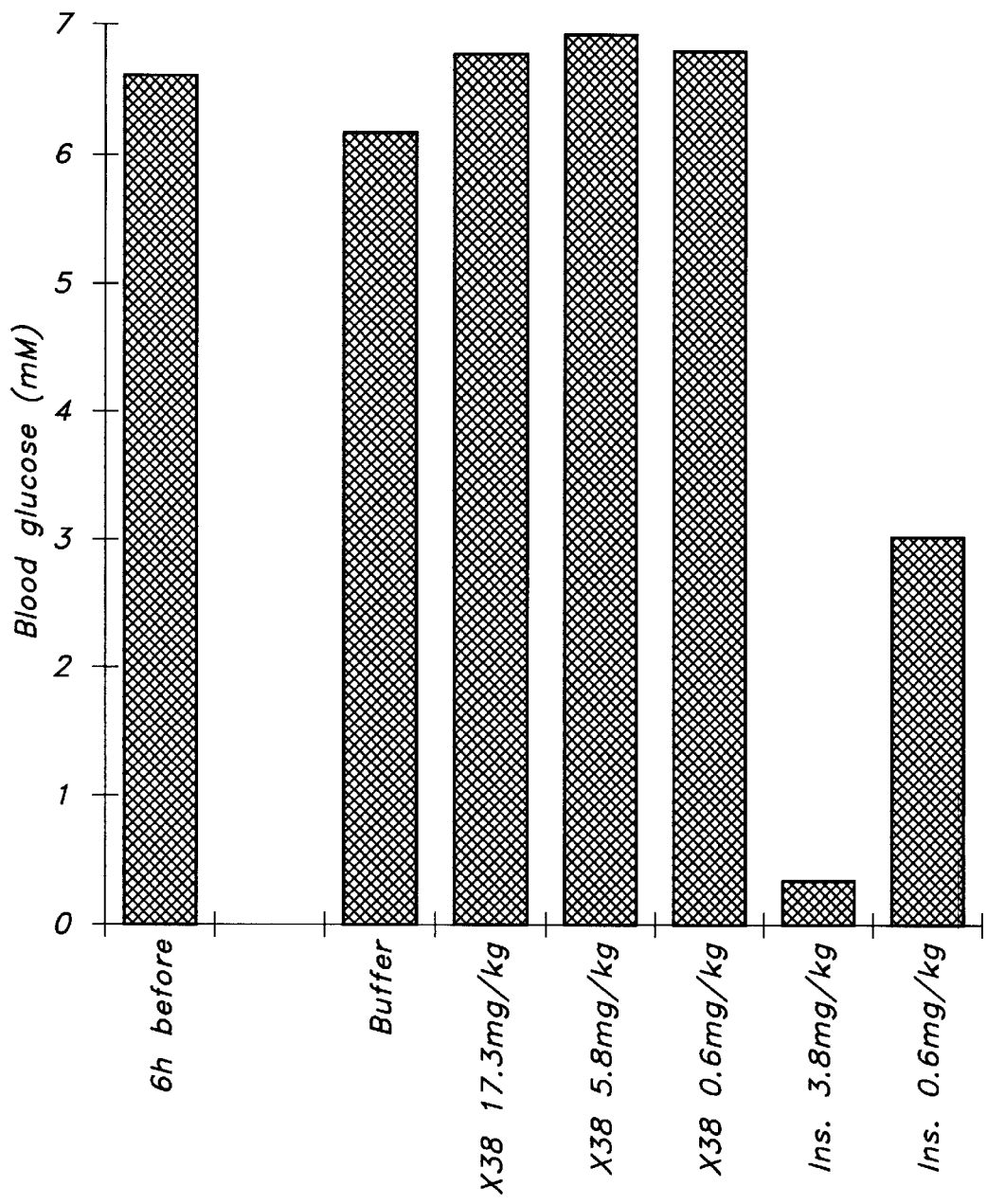

This application is a 35 U.S.C. 371 national application of PCT/DK96/00297 filed Jul. 1, 1996 and claims priority under 35 U.S.C. 119 of Danish application 0765/95 filed Jun. 30, 1995, the contents of which are fully incorporated herein by reference.

FIELD OF THE INVENTION

The present invention relates to the use of an insulin-like polypeptide without hypoglycaemic effect for delaying or preventing the onset of diabetes or for ameliorating an early stage thereof.

BACKGROUND OF THE INVENTION

Autoimmune diseases are characterized by an abnormal immune response (involving either immune system cells or antibodies) directed against normal autologous (self) tissues. Autoimmune diseases afflict huge numbers of individuals throughout the world.

A normal immune system has the capacity to identify and destroy a large variety of foreign invader organisms such as bacteria and viruses. Remarkably, a normal immune system can readily distinguish foreign substances from self, and thereby is able to react vigorously against potentially pathogenic entities from the environment without harming the host's own cells.

The immune system's non-reactivity to self is termed immunological tolerance. In pathological situations, immunological tolerance to a wide variety of self substances is broken, resulting in an autoimmune response. If of an appropriate nature and of sufficient severity and duration, the anti-self response will result in an autoimmune disease. Cellular immune mechanisms are believed to be primarily involved in insulin dependent diabetes (IDD).

Whereas susceptibility to autoimmune diseases may be inherited through the defective actions of multiple genes, indirect evidence suggests that an interaction with a foreign substance from the environment may also be necessary to induce the pathogenic process that results in disease. One explanation for this is that immunization with the foreign inductive chemical induces a cross-reactive response to self through molecular mimicry or chemical similarity. However, once the autoimmune process has been initiated, other secondary immunizing events involving other self antigens typically occur through the release of intracellular constituents in forms not normally encountered by the immune system. Targeted organs thus become damaged through the combination of all of these events, which leads to the appearance of a clinically recognized disorder only when the disease process has progressed to ablate large numbers of tissue cells so targeted.

A number of strategies have been used or proposed to suppress autoimmune diseases, most notably drugs, such as cyclophosphamide, cyclosporin A, methotrexate, and azathioprine. Steroid compounds, such as prednisone and methylprednisolone, are also employed in many instances. These drugs have limited long term efficacy against both cell- and antibody-mediated autoimmune diseases. Use of drugs is limited by virtue of their toxic side effects which include universal immunosuppression. Prolonged treatment with these drugs inhibits the normal protective immune response to pathogenic microorganisms, thereby increasing the risk of infections. A further drawback is that immune-mediated elimination of aberrant cells is impaired and there is, thus, an increased risk that malignancies will develop in patients receiving prolonged global immunosuppression.

Because the subject invention concerns insulin dependent (Type I) diabetes, a detailed background of diabetes is provided below.

Insulin dependent diabetes

Diabetes mellitus comprises a group of diseases that result in elevation of the blood glucose level because of relative or absolute deficiency in the pancreatic hormone insulin. Insulin is secreted into the blood when food is ingested and primarily directs absorbed nutrients into body stores. Diabetes is a major public health problem affecting at least 5 million and as many as 10 million Americans. The prevalence of the most severe form of IDD is 1 in 300 in the United States.

Chronic elevation of the blood glucose level is the most obvious metabolic effect in diabetes and is associated with progressive damage to blood vessels. This may lead to heart attack, stroke, blindness, peripheral nerve dysfunction, and kidney failure. The frequency and severity of diabetes-related complications are greatest in the insulin dependent form of the disease, in which an immunological destruction of the insulin secreting pancreatic beta cells occurs. The high rate of irreversible complications in IDD occurs despite the availability of insulin replacement through injections given 1–4 times daily.

Insulin and other pancreatic hormones are well known and characterized. See, for example, Steiner et al. (1989) "Chemistry and Biosynthesis of Pancreatic Protein Hormones," in Endocrinology; DeGroot et al., EDs., W.B. Saunders Company, p. 1263–1289. As described in Steiner et al., the amino acid sequence of insulin is highly conserved across a number of species, including human, monkey, swine, and ox. IDD has proved itself to be predictable both in unaffected relatives of patients with IDD, as well as in persons from the general population. A predisposition to develop clinical diabetes can be detected through several different tests. For example, genetic susceptibility to diabetes has become increasingly definable through the use of molecular biological means, usually from DNA samples obtained from peripheral blood. One major gene involved in the inherited susceptibility to IDD is that located at the HLA-DQ locus. It is currently possible to identify risks varying from essentially none to those as high as 70 fold above those without the genotype. In families a genetic risk as high as 1 in 4 can be estimated for unaffected siblings just through identification of HLA haplotypes shared with the affected proband.

Persons who have just developed IDD or are in process of developing IDD have a number of disease-specific autoantibodies in their blood. Such autoantibodies include those to islet cell antigens (ICA), to beta cell specific proteins of 64 kDa, which are now believed to be the lower molecular isoform of glutamic acid decarboxylase ($GAD_{65}$), to native insulin and proinsulin, and to a number of more minor determinants such as carboxypeptidase-H and heat shock proteins belonging to the hsp-60 family.

Insulin autoantibodies (IAA) are observed in untreated, newly diagnosed IDD patients (Palmer et al. (1983) Science 222, 1337–1339) as well as in apparently unaffected relatives of diabetic probands. Whereas autoimmunity to insulin could directly cause beta-cell damage, could interfere with the action of endogenous insulin, or could have both effects, some investigators suggested that IAA reflect the rate of islet cell destruction and thus act merely as reporters of aggressive islet directed autoimmunity (Ziegler et al. (1989) Diabetes 38, 1320–1325; Vardi (1988) Diabetes Care 11, 736–739).

The spontaneously diabetic non-obese diabetic (NOD) mouse and the BB rat are useful animal models for human IDD. Analysis of these animals provides important insights into the sequence of pathogenic events, and leads to an understanding of the nature of the autoimmunological process. Previous studies from several laboratories have demonstrated that an extended prophylactic course of daily, subcutaneous injections of high doses of insulin protected NOD mice and BB rat from both hyperglycaemia and islet infiltration by mononuclear leucocytes (insulitis) (Atkinson et al. (1990) Diabetes 39, 933–937, Gotfredsen et al. (1985) Diabetologia 28, 933–935).

In addition, prophylactic treatment with high doses of insulin has been reported to prevent diabetes in NOD mice and in BB rats adoptively transferred with spleen lymphocytes from acutely diabetic animals to their non-diabetic counterparts (Thivolet et al. (1991) Diabetologia 34, 314–319).

Such treatment may relieve the pancreatic beta-cells of metabolic demands and thus induce a state of "beta-cell rest". This quiescent state may be associated with diminished expression of many islet factors, including those that may serve as potential autoantigens at the cell surface (Aaen et al. (1990) Diabetes 39, 697–701; Kämpe et al. (1989) Diabetes 38, 1326–1328). Non-specific immunostimulation caused by cytokine (Jacob et al. (1990) Proc. Natl. Acad. Sci. USA 87, 968–972) or adjuvant (Sadelain et al. (1990) Diabetes 39, 583–589) treatments, or environmental microbes have been implicated in other protocols of IDD prevention (Like et al. (1990) Diabetes 40, 259–262). A better understanding of the pathogenic role of insulin autoimmunity in IDD is clearly required.

There have been reports of efforts to induce antigen-specific immunoregulation to ameliorate autoimmune diseases (Steinman, L. (1990) Mol. Biol. Ned. 7, 333–339) . For example, various methods have been employed to induce antigen-specific suppression of experimental allergic encephalomyelitis (EAE) (PCT publication Wo 91/15225). Recently, several novel immunological approaches have been explored to autoimmune diseases such as EAE in mice and rats and lupus nephritis in MRL/l pr mice. Many have been directed toward blocking the function of the effector $CD4^+$ T cell which has been shown to exhibit $V_\beta$ isotype restriction in EAE. These approaches have included the use of anti-TCR antibodies (Archa-Orbea et al., supra), synthetic TCR peptides (Offner et al. (1991) Science 251, 430–432) and superantigen treatment (Kim et al. (1991) J. Exp. Ned. 174, 1431–1437). The tolerogenic effects of enteral or pulmonal administration of antigens have also been described (Silverman et al. (1983) J. Immunol. 131, 2651–2661; Peng et al. (1990) Clin. Exp. Immunol. 81, 510–515; Michael (1989) Immune Invest. 18, 1049–1054; Kitamura et al. (1987) J. Immunol. 139, 3251–3259; Michalek et al. (1982) J. Immuno. 128, 1992–1998; Mowat et al. (1986) Immunol. 58, 677–683; PCT publications WO 91/12816, WO 91/01333; WO 92/06704). Nagler-Anderson et al. (1986) Proc. Natl. Acad. Sci. USA 83, 7443–7446 describe the suppression of arthritis by oral administration of soluble type II collagen in a collagen-induced arthritis mouse model. Deficiencies in this ability have been reported in several experimental mouse models of autoimmune diseases (Gesualdo et al. (1990) J. Inmaunol. 145, 3684–3691; Miller et al. (1984) Clin. Immunol. Immunopathol. 31, 231–240).

Zhang et al. have in NOD mice observed a reduced frequency of diabetes in response to very high doses of oral insulin (Zhang et al. (1991) Proc. Natl. Acad. Sci. USA 88, 10252–10256) and further demonstrated in co-transfer studies that splenocytes from insulin-fed NOD mice prevented the adoptive transfer of diabetes by splenocytes from untreated diabetic mice to irradiated recipients.

In contrast, oral administration of insulin to spontaneously or induced diabetes-prone BB rats was reported not to offer any protection against diabetes (Mordes et al., 1995, The New York Academy of Science, "Oral Tolerance: Mechanism and Application").

Muir et al. (PCT publication WO 94/23737) have reported that, in NOD mice, administration of human insulin or its B-chain together with a powerful immune-stimulating adjuvant provides a small but significant protection against diabetes. This protection can be adoptively transferred to irradiated NOD mice co-infused with diabetogenic spleen cells and is associated with a reduced expression of gamma-interferon in the islet infiltrating lesion.

Also in the NOD mouse, nasal administration of insulin or a fragment of its B-chain has been reported to protect against diabetes adoptively transferred to non-diabetic NOD mice with a diabetogenic NOD T cell clone reactive against an amino acid sequence harboured in the insulin B-chain fragment referred to above or against spontaneous diabetes in NOD mice (Wegman et al. (1995) The New York Academy of Science, "Oral Tolerance: Mechanism and Application").

In yet another example of the use of insulin in the protection against diabetes, it has been reported that a single intravenous injection of insulin into NOD mice is followed by a reduced incidence of diabetes compared to non-treated animals.

The above examples of using insulin for preventing the onset of clinical diabetes have all been carried out in animal models of IDD, i.e. the NOD mouse and BB rat, but there is an increasing evidence that the same phenomena occur in the case of human IDD. Thus, fewer individuals, at high risk of developing IDD based on family history and immune markers, that were treated in the non-diabetic state with daily s.c. injections of insulin developed IDD than untreated individuals at a comparable high risk. Currently, large clinical studies in the US and in Europe are undertaken to formally prove whether prophylactic insulin therapy in non-diabetic, at-risk individuals can protect against subsequent development of IDD.

The mechanism whereby insulin exerts its effect in protecting against diabetes are not known exactly, but two issues are common to the above mentioned examples of the prophylactic use of insulin. One is that in most cases hormonally active insulin has been used in doses sufficient to cause constant or transient hypoglycaemia. In fact, the doses used in the animals studies have often led to high frequencies of deaths due to hypoglycaemia and the doses used in humans are of a magnitude where hypoglycaemic symptoms may frequently be expected.

The other common issue is the fact that a non-hormonal, immunologic protective mechanism of insulin, e.g., nasal administration of insulin B-chain fragment, relies on the use of a genetically homogenous animal strain. The immune response to an antigenic stimulus, whether of immunizing or tolerogenic nature, occurs via the presentation of a peptide fragment of the protein antigen in question to T cells. The peptide is presented on a cellular receptor, the MHC (major histocompatibility) molecules. The MHC molecules are extremely polymorphic, thus two classes of molecules exist, class I and class II and within each class several loci exist, e.g., the HLA class I (A, B and C loci) and HLA class II (DR, DQ and DP) in humans, and within each locus a large number of polymorphic alleles exist. Different MHC molecules present different peptides to T cells, even from the same antigen. Consequently, to obtain a T cell response, be it immunogenic or tolerogenic, to a given antigen, e.g., insulin in an outbred, MHC polymorphic population like humans, administration of the entire antigen, or at least the major part of it is likely to be required to obtain the desired response in all or most individuals treated.

According to the present invention, an insulin-like polypeptide without hypoglycaemic effect is used to prevent against the development of diabetes. The insulin is rendered hormonally inactive by discrete, specified deletions or amino acid substitutions which leaves the insulin minimally changed or as a fragment of the endogenous molecule. The present invention makes possible the treatment of clinical healthy individuals, albeit at a certain risk of developing a serious disease, with a disease specific antigen, insulin, without exposing the individual to the potential serious adverse effects, hypoglycaemia and mitogenicity secondary to the actions of hormonally active insulin. In an example of the present invention, daily sc injections with human insulin with a single amino acid substitution in position B25 that renders the molecule less than 0.1% hormonally active, in NOD mice protects as well against diabetes as equimolar doses of human insulin does, but without the adverse effects of insulin, i.e., approx. 50% deaths due to hypoglycaemia.

SUMMARY OF THE INVENTION

In one aspect, the present invention concerns insulin molecules rendered hormonally inactive by specific deletions and/or amino acid substitutions for the prevention, delay in the onset of, or early amelioration of type 1 diabetes in a mammal, in particular a human being, at risk of developing said disease.

In another aspect, the present invention concerns naturally occurring insulins which are hormonally inactive in mammals, in particular in human beings for the prevention, delay in the onset of, or early amelioration of type 1 diabetes in a mammal, in particular in a human being.

In a further aspect, the present invention relates to a pharmaceutical composition comprising a hormonally inactive insulin.

In a still further aspect, the present invention relates to the use of a hormonally inactive insulin for producing a pharmaceutical composition for preventing or delaying the onset of a disease having the characteristics of type 1 diabetes or for ameliorating an early stage thereof in a mammal, in particular a human being, at risk of developing said disease.

As used in the present description, the expression "a hormonally active insulin" designates a naturally occurring insulin or an insulin analogue with a biological activity (hypoglycaemic effect) which makes it potentially useful in the treatment of manifest type 1 diabetes in a mammal, particularly in a human being.

As used in the present description, the expression "a hormonally inactive insulin" designates a naturally occurring insulin or an insulin analogue with a biological activity (hypoglycaemic effect) which is so low that it cannot be considered as potentially useful in the treatment of manifest type 1 diabetes in a mammal, particularly in a human being. According to the present invention, such hormonally inactive insulins have an in vitro activity which is less than 7%, preferably less than 3%, more preferred less than 1%, still more preferred less than 0.1% of the activity exhibited by human insulin when tested in either the mouse free fat cell assay as described by Vølund et al. (1991) Diabetic Medicine 8, 839–847 with reference to Moody et al. (1974) Horm. Metab. Res. 6, 12–16 and Vølund (1978) Biometrics 34, 357–365 or in the receptor binding assay as described by Andersen et al. (1992) J. Biol. Chem. 267, 13681–13686.

In the present specification, whenever the term insulin is used in a plural or a generic sense it is intended to encompass both naturally occurring insulins and insulin analogues unless otherwise specified. By "insulin analogue" as used herein is meant a polypeptide having a molecular structure similar to that of human insulin including the disulphide bridges between $Cys^{A7}$ and $Cys^{B7}$ and between $Cys^{A20}$ and $Cys^{B19}$ and in most cases also an internal disulphide bridge between $Cys^{A6}$ and $Cys^{A11}$. Hormonally inactive insulins can formally be derived from human insulin by deleting and/or substituting a moderate number of amino acid residues. In the insulin analogues of the present Table 1 the sum of the number of deletions and substitutions is not higher than 7.

In one preferred embodiment, the insulin analogues of the invention contain no deletions and only two substitutions.

In another preferred embodiment, the insulin analogues of the invention contain no deletions and only one substitution.

Specifically exemplified in the present examples is the use of a human insulin analogue, $Asp^{B25}$ human insulin, to effectively protect against the development of IDD. The hormonally inactive insulins disclosed herein effectively block or immunologically override the autoimmune reaction that causes destruction of the insulin-secreting cells of the pancreas, without exposing the treated individuals to the adverse effects of insulin therapy.

Treatment with compositions of the subject invention obviates the need for daily insulin therapy, the need for repeated blood glucose monitoring, and the restrictions of diet and exercise imposed upon all patients with IDD receiving insulin replacement therapy. Further, and most importantly, the complications of IDD, which are directly attributable to the duration and severity of overt diabetes and hyperglycaemia, will be inhibited. Those who would be likely to benefit most from the treatment would be those with a high genetic risk profile, such as a five-fold or greater risk as determined by HLA and/or other genotyping studies, as well as those found to have a high predictive profile as determined through specific autoantibody analysis, e.g., $GAD_{65}$ autoantibodies.

BRIEF DESCRIPTION OF THE DRWINGS

The present invention is further illustrated with reference to the appended drawings wherein FIG. 1 shows the effect on the blood glucose level of daily injections of buffer, various doses of $Asp^{B25}$ human insulin (code: X38) and various doses of human insulin, respectively;

FIG. 2 is a graph showing the effects of subcutaneous administration of human insulin, $Asp^{B25}$ human insulin (code: X38) and buffer on diabetes in NOD mice;

FIG. 3 is a graph showing the effects of subcutaneous administration of human insulin, $Asp^{B25}$ human insulin (code: X38) and buffer on survival in NOD mice;

FIG. 4 is a graph showing the effects of subcutaneous administration of insulin, $Asp^{B25}$ human insulin (code: X38) and buffer in the initial stages of diabetes in NOD mice; and FIG. 5 is a graph showing the effects of oral administration of insulin or buffer on blood glucose levels in NOD mice.

DETAILED DESCRIPTION OF THE INVENTION

The subject invention concerns insulin compositions uniquely suited for use in new, clinically important, immunomodulating therapies that selectively inhibits beta-cell destructive immune responses without inducing insulin inherent side effects and a state of generalized immunosuppression replete with its serious side effects. The use of the insulin compositions of the subject invention represent an important advance in the development of preventive, interventive or ameliorating therapies for diabetes.

Another critical distinguishing feature of the subject invention is the use of insulin before the appearance of clinical symptoms of IDD. Clearly, because of the metabolic activities of insulin, it is not common practice to administer insulin unless there is already clinical evidence of pancreatic islet cell destruction and insulin insufficiency. According to the subject invention, however, modified insulin or a fragment thereof, is best administered before any symptoms appear.

Methods of analysing the biological activity (hypoglycaemic effect) of insulins are well know, and include receptor binding assays using whole cells or soluble receptors, the mouse free fat cell assay, euglycaemic pig clamp assay, intravenous rabbit blood glucose assay and the subcutaneous mouse blood glucose assay (Vølund et al. (1991) Diabetic Medicine, 8, 839–847, Brange et al. (1990) Diabetes Care 13, 923–954, Drejer (1992) Diabetes/Metabolism Reviews 8, 259–286).

In a preferred embodiment, the insulin analogues of the invention are selected from the insulin analogues listed in Table 1. The biological activities stated in Table 1 are given relative to human insulin (=1.00) using either receptor binding or lipogenesis assays.

TABLE 1

| Insulin analogue | Activity relative to human insulin (=1.00) |
| --- | --- |
| desA1 human insulin; | 0.006 |
| des(A1–A2) human insulin; | 0.0014 |
| des(A1–A3) human insulin; | 0.0011 |
| desA21 human insulin; | 0.04 |
| des(B1–B5) human insulin; | 0.05 |
| des(B1–B6) human insulin; | 0.0004 |
| des(B23–B30) human insulin; | 0.001 |
| des(B24–B30) human insulin; | 0.002 |
| des(B25–B30) human insulin; | 0.06 |
| $Gly^{A2}$ human insulin; | 0.01 |
| $Ala^{A2}$ human insulin; | 0.006 |
| $Nle^{A2}$ human insulin; | 0.01 |
| $Thr^{A2}$ human insulin; | 0.001 |
| $Pro^{A2}$ human insulin; | 0.01 |
| D-allo $Ile^{A2}$ human insulin; | 0.002 |
| $Nva^{A3}$ human insulin; | 0.014 |
| $Nle^{A3}$ human insulin; | 0.0038 |
| $Leu^{A3}$ human insulin; | 0.0018 |
| $Val^{A2}$, $Ile^{A3}$ human insulin; | 0.021 |
| $Abu^{A2}$, $Abu^{A3}$ human insulin; | 0.0041 |
| $Gly^{A2}$, $Gly^{A3}$ human insulin; | 0.00014 |
| D-$Cys^{A6}$ human insulin; | 0.0023 |
| D-$Cys^{A6}$, D-$Cys^{A11}$ human insulin; | 0.00027 |
| $Ser^{A6}$, $Ser^{A11}$, des(A8–A10) human insulin; | 0.0001 |
| D-$Cys^{A7}$ human insulin; | 0.002 |
| D-$Cys^{A11}$ human insulin; | 0.007 |
| $Leu^{A19}$ human insulin; | 0.001 |
| $Gly^{B6}$ human insulin; | 0.0005 |
| $Glu^{B12}$ human insulin; | 0.0004 |
| $Asn^{B12}$ human insulin; | 0.002 |
| $Phe^{B12}$ human insulin; | 0.002 |
| D-$Ala^{B12}$ human insulin; | 0.007 |
| $Asp^{B25}$ human insulin (code: X38). | 0.001 |

The insulin analogues of the present invention can be prepared by methods known per se, see for example Märki et al. (1979) Hoppe-Seyler's Z. Physiol. Chem. 360, 1619–1632; Kitagawa et al. (1984) Biochemistry 23, 4444–4448; Schwartz et al. (1978) Biochemistry 17, 4550–4556; Nakagawa et al. (1991) J. Biol. Chem. 266, 11502–11509; Schwartz et al. (1981) Int. J. Pept. Protein Res. 17, 243–255; Hu et al. (1993) Biochemistry 32, 2631–2635; Nakagawa et al. (1986) J. Biol. Chem. 261, 7332–7341; and Riemen et al. (1983) Biochemistry 22, 1507–1515.

Pharmaceutical compositions

Pharmaceutical compositions containing an insulin analogue according to the present invention may be administered orally or parenterally to a person in need of such a treatment. Parenteral administration may be performed by subcutaneous, intramuscular or intravenous injection by means of a syringe, optionally a pen-like syringe. Alternatively, parenteral administration can be performed by means of an infusion pump or a needleless injection device. A further option is to administer a composition which may be a powder or a liquid containing the insulin analogue in the form of a nasal spray. As a still further option, it may also be possible to administer the insulin analogue transdermally.

Pharmaceutical compositions containing an insulin analogue of the present invention may be prepared by conventional techniques, e.g. as described in *Remington's Pharmaceutical Sciences* (1985).

Thus, an injectable composition of an insulin analogue of the invention can be prepared using the conventional techniques of the pharmaceutical industry which involves dissolving and mixing the ingredients as appropriate to give the desired end product.

According to one procedure, the insulin is dissolved in a volume of water which is somewhat below the final volume of the composition to be prepared. An isotonic agent, a preservative, a buffer and optionally other auxiliary agents are added as required and the pH value of the solution is adjusted—if necessary—using an acid, e.g. hydrochloric acid, or a base, e.g. aqueous sodium hydroxide, as needed. Finally, the volume of the solution is adjusted with water to give the desired concentration of the ingredients.

Examples of isotonic agents are sodium chloride, mannitol and glycerol.

Examples of preservatives are phenol, m-cresol, methyl p-hy-droxybenzoate and benzyl alcohol.

Examples of suitable buffers are sodium acetate, sodium citrate and sodium phosphate. Certain of the above-mentioned auxiliary agents may also be added in order to improve the stability of the composition. Typically, the insulin analogues of the invention are present in the compositions in the form of zinc complexes which may contain from about 0.25 to about 0.75 zinc ions per insulin monomer. Such complexes may further contain phenol and/or m-cresol.

According to one preferred aspect of the present invention, there is provided a pharmaceutical composition of an insulin analogue of the invention in the form of a solution containing hexameric complexes of the said analogue. Typically the hexameric complexes are stabilized by two or more zinc ions and three or more molecules of a phenolic compound like phenol or m-cresol or mixtures thereof per hexamer.

A composition for nasal administration of an insulin analogue may, for example, be prepared as described in European Patent No. 272097 (to Novo Nordisk A/S).

The insulin analogues of this invention can be used in the prevention of diabetes. The particular insulin analogue to be used and the optimal dose level for any patient will depend on a variety of factors including the efficacy of the specific insulin analogue employed, the age, body weight, physical activity, and diet of the patient and on a possible combination with other drugs. It is recommended that the dosage of the insulin analogue of this invention be determined for each individual patient by those skilled in the art.

The present invention is further illustrated by the following examples which, however, are not to be construed as limiting in any way the claimed scope of protection of the invention. The features disclosed in the foregoing description and in the following examples may, both separately and in any combination thereof, be material for realizing the invention in diverse forms thereof.

EXAMPLES

Units of insulin have been converted to mg by using the equation 26 U=1 mg.

EXAMPLE 1

Effect on the blood glucose level of daily administration of $Asp^{B25}$ human insulin to NOD mice.

Groups of 5 female NOD mice (from Bommice, Bomholtgård, Ry, Denmark), 9 weeks old were treated daily, 7 days a week, for 26 days with subcutaneous injection of either buffer, human insulin (3.8 mg/kg body weight or 0.6 mg/kg) or $Asp^{B25}$ human insulin (code: X38) (17.3 mg/kg, 5.8 mg/kg or 0.6 mg/kg). On day seven, an initial blood glucose value was determined at 7:00 am, the injection was given at 7:45 and a further determination of the blood glucose value was made 6 hours later. The results are summarised FIG. 1 which clearly demonstrates that even extremely high doses of X38 do not affect the blood glucose levels. In contrast, insulin (0.6 mg/kg) has a marked hypoglycaemic effect. Furthermore, 4 of the 5 animals receiving insulin (3.8 mg/kg) died of hypoglycaemia after 3–5 days of treatment and animal number five had to be sacrificed on day seven due to symptoms of hypoglycaemia. None of the mice treated with X38, even in the extremely high doses died or displayed hypoglycaemia during the 26 days observation period.

EXAMPLE 2

Prophylactic effect of daily administration of $Asp^{B25}$ human insulin to NOD mice.

Female NOD (non-obese diabetic) mice, 4 weeks old, were obtained from Bommice (Bomholtgård, Ry, Denmark). At the beginning of the experiment there were a total of 30 animals in each of the three groups mentioned below. From 5 weeks of age the animals were injected daily for 7 days a week, with either human insulin (Protaphane®, Novo Nordisk A/S, Denmark) 0.77 mg/kg body weight of a 0.15 mg/ml preparation, $Asp^{B25}$ human insulin (code: X38) 0.77 mg/kg body weight of a 0.15 mg/ml preparation or an equal volume of the buffer used for diluting the Protaphane® insulin. The treatment was continued until the mice were 32 weeks old, at which age treatment was stopped and the mice observed until they were 40 weeks old. Beginning when the mice were 10 weeks old, the urine was tested weekly for the presence of glucose using glucosuria test tape (Tes-Tape, Lilly, Indianapolis, Ind.). If an animal tested positive in the glucose urine test, a blood sample was taken and blood glucose measured using a glucose analyzer. If the blood glucose was 15 mmol/l or higher, the animal was classified as diabetic and then sacrificed.

Figure 2:
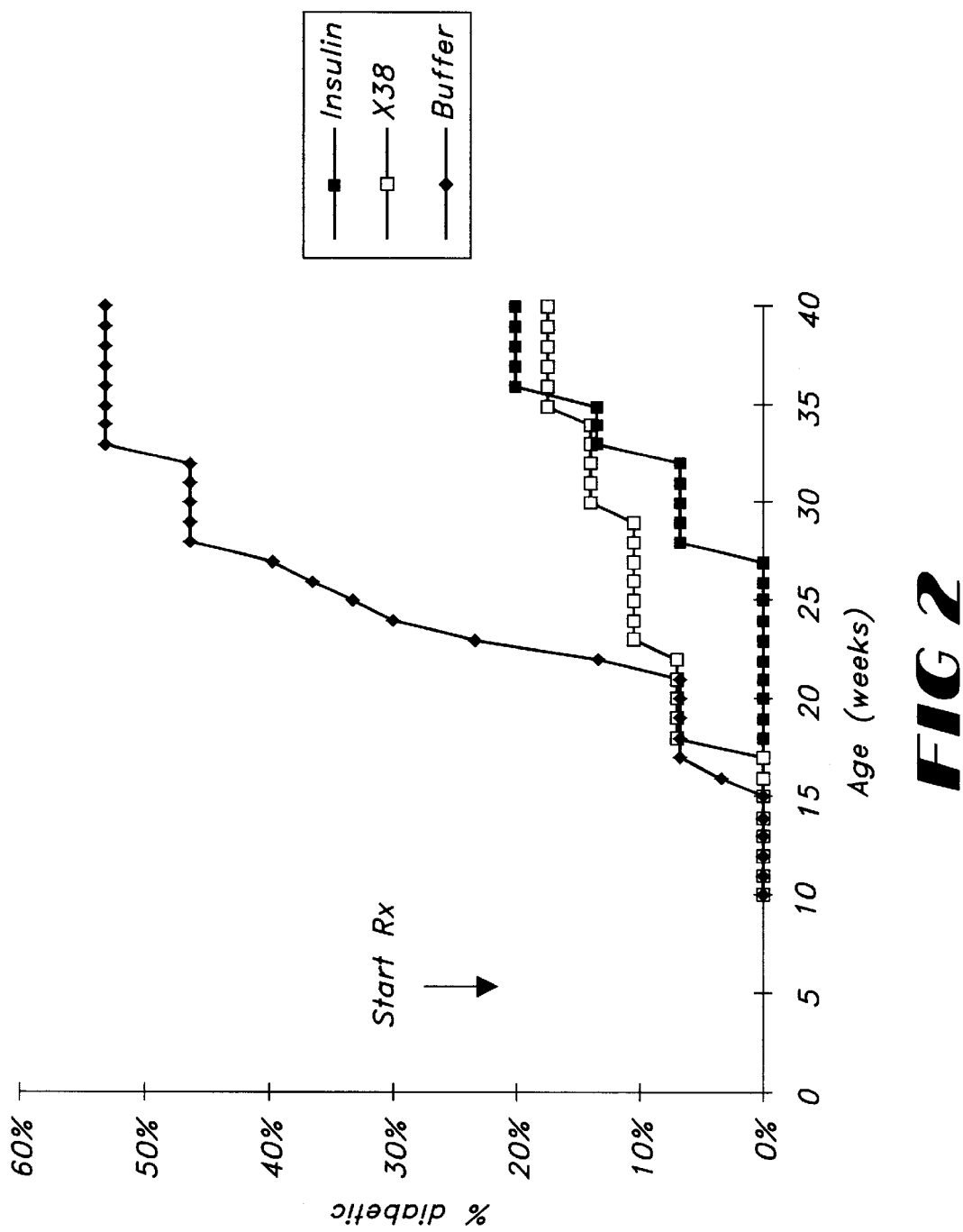

As shown in FIG. 2, a high proportion of the buffer treated animals developed diabetes at an incidence and age at onset similar to that observed in the parent female NOD mouse colony and as reported in the literature. Daily treatment with insulin from 5 weeks of age in doses as previously reported (Atkinson et al. (1990) Diabetes 39, 933–937, Gotfredsen et al. (1985) Diabetologia 28, 933–935), significantly reduced the incidence of diabetes ($p<0.05$) at 31 weeks of age. Termination of treatment was not followed by an abrupt increase in diabetes incidence, and at 40 weeks of age the incidence was still significantly ($p<0.05$) lower than in the buffer treated animals. Surprisingly, daily injections of X38 prevented the development of diabetes to the same, or higher degree as insulin did. Thus, at 31 weeks of age after 26 weeks of treatment, the diabetes incidence was highly significantly ($p<0.01$) lower in the X38 treated animals than in the buffer treated, but not different from that in the insulin treated group. After termination of treatment only 1 case of diabetes occurred, thus at 40 weeks of age the diabetes incidence in the X38 treated animals was still highly significantly lower than in the buffer treated group ($p<0.01$). At onset of diabetes in these NOD mice, blood glucose values are typically 20 mmol/l or higher. At the end of the experiment, the blood glucose values were determined in non-diabetic animals and all were in the range of 7–10 mmol/l (data not shown). Three times during the treatment period, treatment was discontinued for one day and blood glucose values determined 48 hours after the last injection with insulin, X38 or buffer. No previously non-diabetic animals turned out as diabetic following the temporary discontinuation of the treatment. Thus, the treatment was not simply masking hyperglycaemia.

Figure 3:
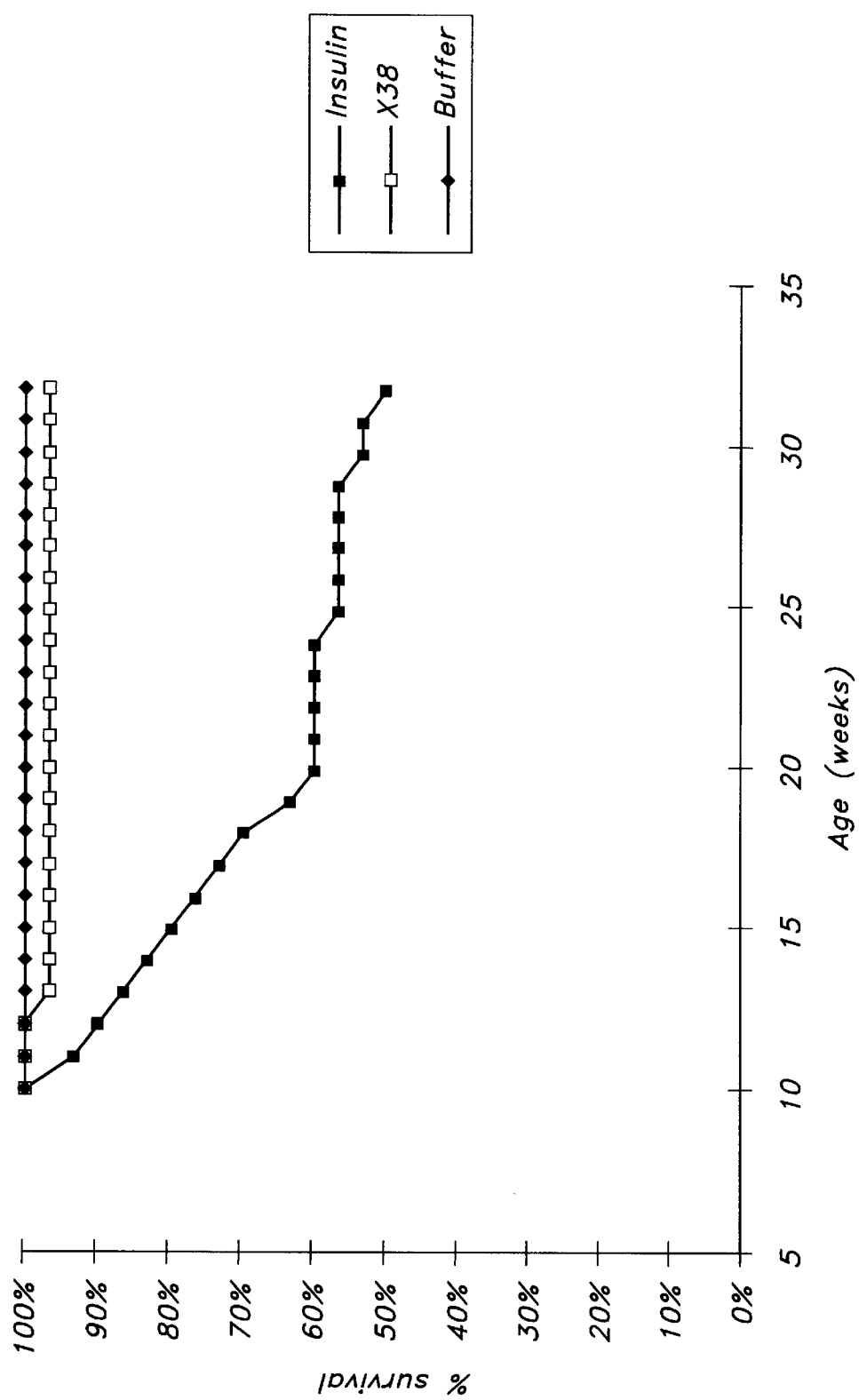

A previous study (Atkinson et al. (1990) Diabetes 39, 933–937) has shown that for prophylactic subcutaneous insulin to be active, high sublethal doses are required. FIG. 3 confirms this observation, since 50% of the insulin treated mice died of hypoglycaemia during the treatment period. In contrast, even though X38 provided the same protection against the development of diabetes as insulin did, only one X38 treated animal died. This is not statistically different from the result in the buffer treated group.

These results demonstrate that diabetes can be prevented using a hormonally inactive insulin analogue without the adverse effects of continuous hypoglycaemia due to insulin treatment.

EXAMPLE 3

Effect on diabetes of daily, prophylactic administration of $Asp^{B25}$ human insulin in the initial stage of diabetes in NOD mice.

Female NOD (non-obese diabetic) mice, 4–5 weeks old, were obtained from the Jackson Laboratory (Bar Harbour, Me.). At the beginning of the experiment, there were a total of 20 animals in each of the three groups mentioned below. From 10 weeks of age, at an age where there are manifest signs of cellular infiltration in the islets of Langerhans and beginning beta cell destruction and by which age blood glucose levels are at hyperglycaemic concentrations in a certain percentage of animals prior to the onset of diabetes, the animals were injected daily for 7 days a week, with either human insulin (Protaphane® Novo Nordisk A/S, Denmark), 0.77 mg/kg body weight of a 0.15 mg/ml preparation, $Asp^{B25}$ human insulin (code: X38), 0.77 mg/kg body weight of a 0.15 mg/ml or an equal volume of the buffer used for diluting the Protaphane® insulin. The treatment was continued until the mice were 37 weeks old, at which age treatment was stopped. The mice were observed until they were 39 weeks old. Beginning when the mice were 10 weeks old, the urine was tested weekly for the presence of glucose using glucosuria test tape (Tes-Tape, Lilly, Indianapolis, Ind.). If an animal tested positive in the glucose urine test, a blood sample was taken and blood glucose measured using a glucose analyzer. If the blood glucose was 15 mmol/l or higher, the animal was classified as diabetic and sacrificed.

Figure 4:
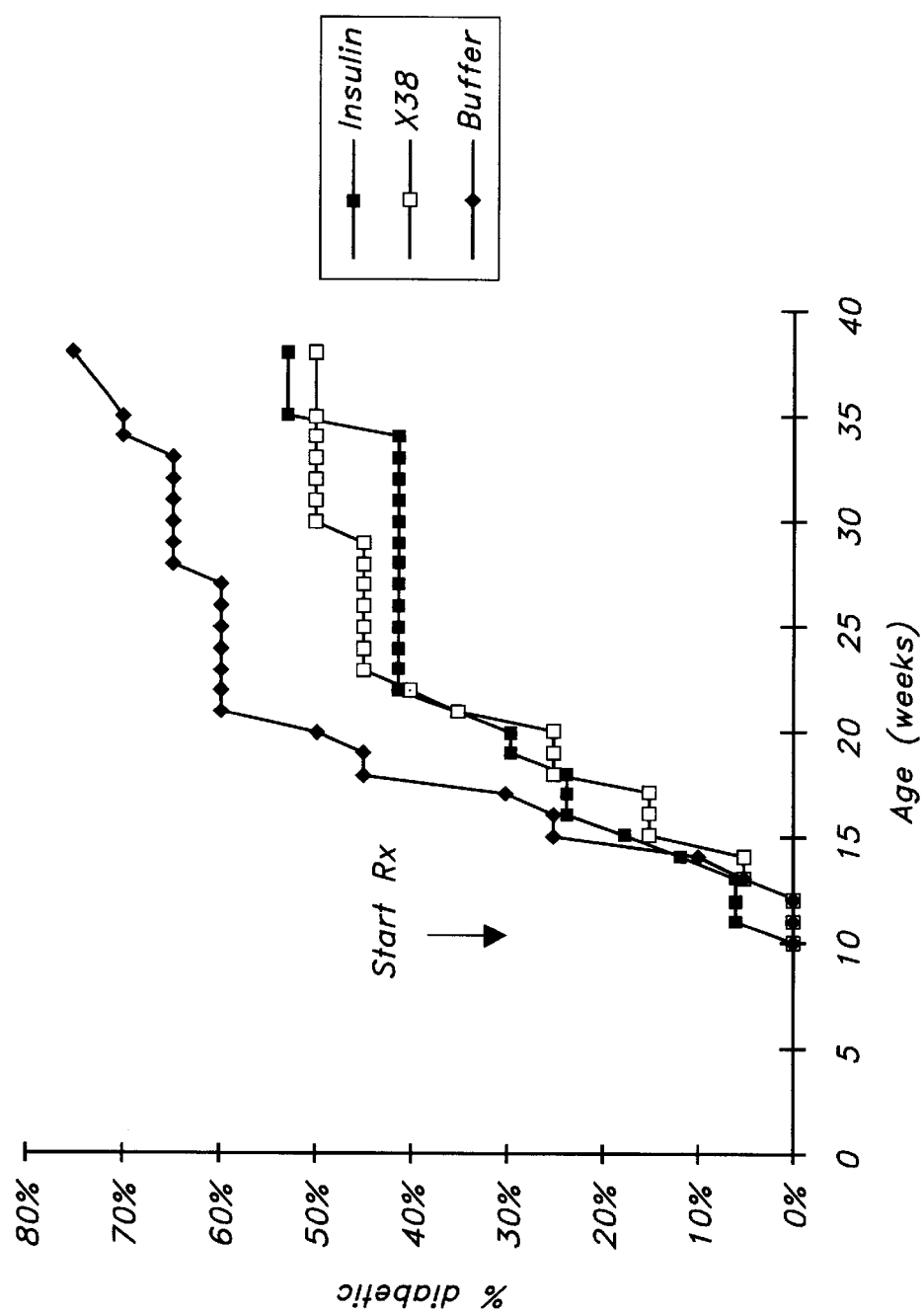

As shown in FIG. 4, a high proportion of the buffer treated animals developed diabetes with a frequency similar to that in other female NOD mice from the same colony. Daily treatment with insulin from the age of 10 weeks reduced the frequency of diabetes compared to buffer treated and untreated animals. This effect was demonstrable from the age of 15 weeks and persisted until the experiment was terminated. Surprisingly, daily injections of X38 reduced the frequency of diabetes to the same, or higher degree as insulin did in the same age interval. After termination of the treatment, no cases of diabetes occurred in the insulin or X38 treated groups of mice. At the onset of diabetes in these NOD mice, blood glucose values were typically 20 mmol/l or higher. At the end of the experiment, the blood glucose values were determined in non-diabetic animals and all were in the range of 7–10 mmol/l (data not shown). Three times during the treatment period, treatment was discontinued for one day and blood glucose values determined 48 hours after the last injection of insulin, X38 or buffer. No previously non-diabetic animals turned out as diabetic following the temporary discontinuation of the treatment Thus, the treatment was not simply masking hyperglycaemia.

In the group of insulin treated mice, 15% died of hypoglycaemia during the treatment period. In contrast, even though X38 provided the same protection against the development of diabetes as insulin did, none of the X38 treated animals died. None of the buffer treated animals died in the observation period.

EXAMPLE 4

Effect of oral administration of $Asp^{B25}$ human insulin on the blood glucose level in NOD mice.

Figure 5:
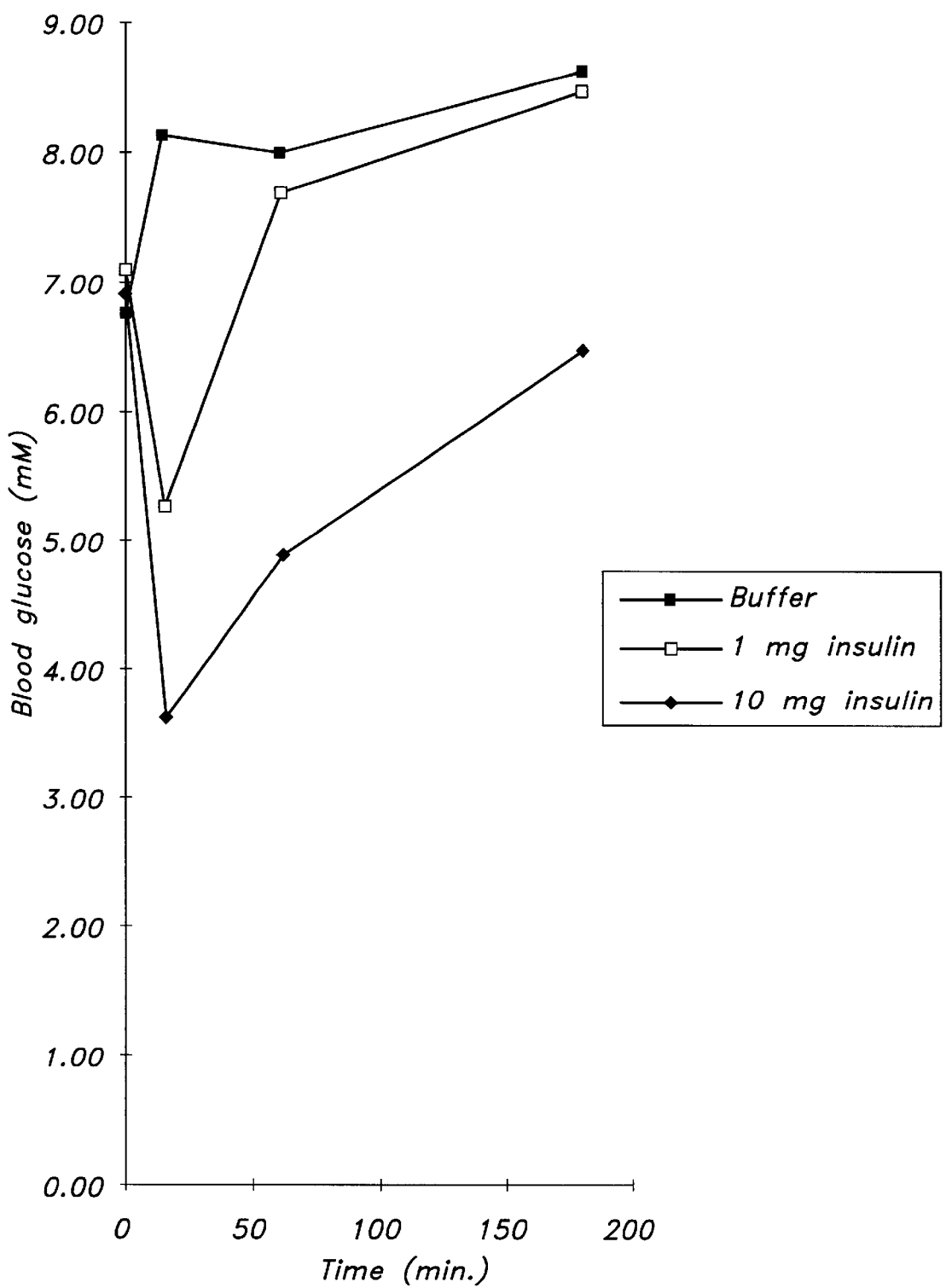

Oral administration of insulin to NOD mice has been reported to prevent diabetes but not to have any effect on the blood glucose level and hence any direct mitogenic effect in the gut milieu (WO 92/06704). Groups of 10 C57/BL mice (from Bommice, Bomholtgård, Ry, Denmark), 5 weeks old, were fed either buffer, 1 mg of human insulin or 10 mg of human insulin 2 times a week for 5 weeks. After 4 weeks of treatment, the effect on the blood glucose level in non-fasted animals was analyzed. An initial blood sample was taken in order to determine the control blood glucose level. 15–30 minutes later the animals were fed by gavage and the blood glucose level was determined after further 15, 60 and 180 minutes. FIG. 5 clearly shows an profound immediate reduction in the blood glucose level after feeding 1 mg insulin, while at 60 minutes blood glucose level was similar to that of the buffer treated animals. Feeding of a higher dose, 10 mg insulin had an even more profound effect that lasted for the duration of the experiment. These data demonstrate two important points: 1) Oral administration of insulin has a profound hypoglycaemic effect which is not desirable in a preventive treatment and which in itself is a well known risk factor. 2) The fact that sufficient insulin is present in the gut to provoke a hypoglycaemic response demonstrates that a high concentration of intact insulin is present in the gut.

Insulin is a well known growth factor and has a direct mitogenic effect. The consequence of having a high concentration of intact insulin in the gut lumen directly exposing gut epithelium to its effect is not known but could potentially be serious.

EXAMPLE 5

A pharmaceutical composition comprising a solution of 600 nmol/ml of $Asp^{B25}$ human insulin, 0.5 zinc ion per insulin monomer, 16 mM m-cresol, 16 mM phenol, 1.6% of glycerol, 23 mM sodium chloride and 7 mM sodium phosphate.

1.2 μmol of $ASp^{B2}$ human insulin was dissolved in water (0.5 ml) by addition of 30 μl 0.2 M hydrochloric acid to pH 2.5–3.0 and 60 μl of 0.01 M zinc acetate was added. To the solution was further added 100 μl of 0.32 M phenol, 200 μl of 0.16 M m-cresol, 400 μl of 8% glycerol, 67 μl of 0.6 M sodium chloride, and pH value of the solution was adjusted to 7.5 by addition of 0.2 M sodium hydroxide. Finally 140 μl of 0.1 M sodium phosphate (pH 7.5) was added and the volume adjusted to 2 ml with water.

What is claimed is:

1. A method of treating type 1 diabetes in a mammal at risk of developing type 1 diabetes, which method comprises administering parenterally to said mammal a pharmaceutical composition consisting essentially of an effective amount of a hormonally inactive insulin analogue selected from the group consisting of desA1 human insulin, des(A1–A2) human insulin, des(A1–A3) human insulin, desA21 human insulin, des(B1–B5) human insulin, des(B1–B6) human insulin, des(B24–B30) human insulin, des(B25–B30) human insulin, $Gly^{A2}$ human insulin, $Ala^{A2}$ human insulin, $Nle^{A2}$ human insulin, $Thr^{A2}$ human insulin, $Pro^{A2}$ human insulin, D-allo $Ile^{A2}$ human insulin, $Nva^{A3}$ human insulin, $Nle^{A3}$ human insulin, $Leu^{A3}$ human insulin, $Val^{A2},Ile^{A3}$ human insulin, $Abu^{A2},Abu^{A3}$ human insulin, $Gly^{A2},Gly^{A3}$ human insulin, $D-Cys^{A6}$ human insulin, $D-Cys^{A6},D-Cys^{A11}$ human insulin, $Ser^{A6},Ser^{A11},$des(A8–A10) human insulin, $D-Cys^{A7}$ human insulin, $D-Cys^{A11}$ human insulin, $Leu^{A19}$ human insulin, $Gly^{B6}$ human insulin, $Glu^{B12}$ human insulin, $Asn^{B12}$ human insulin, $Phe^{B12}$ human insulin, $D-Ala^{B12}$ human insulin, and $Asp^{B25}$ human insulin.

2. The method of claim 1 whwein the mammal is a human being.

3. The method of claim 1 wherein the in vitro activity of the insulin analogue is less than 7% of the activity of human insulin.

4. The method of claim 1, wherein the insulin analogue is $Asp^{B25}$ human insulin.

5. A method of ameliorating type 1 diabetes in a mammal comprising parenterally administering to the mammal an effective amount of a hormonally inactive insulin analogue selected from the group consisting of: desA1 human insulin, des(A1–A2) human insulin, des(A1–A3) human insulin, desA21 human insulin, des(B1–B5) human insulin, des (B1–B6) human insulin, des(B24–B30) human insulin, des (B25–B30) human insulin, $Gly^{A2}$ human insulin, $Ala^{A2}$ human insulin, $Nle^{A2}$ human insulin, $Thr^{A2}$ human insulin, $Pro^{A2}$ human insulin, D-allo $Ile^{A2}$ human insulin, $Nva^{A3}$ human insulin, $Nle^{A3}$ human insulin, $Leu^{A3}$ human insulin, $Val^{A2},Ile^{A3}$ human insulin, $Abu^{A2}$ $Abu^{A3}$ human insulin, $Gly^{A2}Gly^{A3}$ human insulin, $D-Cys^{A6}$ human insulin, $D-Cys^{A6}$ $D-Cys^{A11}$ human insulin, $Ser^{A6}$ $Ser^{A11}$ des (A8–A10) human insulin, $D-Cys^{A7}$ human insulin, $D-Cys^{A11}$ human insulin, $Leu^{A19}$ human insulin, $Gly^{B6}$ human insulin, $Glu^{B12}$ human insulin, $Asn^{B12}$ human insulin, $Phe^{B12}$ human insulin, $D-Ala^{B12}$ human insulin, and $Asp^{B25}$ human insulin.

6. The method of claim 5 wherein the mammal is a human being.

7. The method of claim 5 wherein the in vitro activity of the insulin analogue is less than 7% of the activity of human insulin.

8. The method of claim 5 wherein the insulin analogue is $Asp^{B25}$ human insulin.

* * * * *